United States Patent [19]
Okamoto et al.

[11] Patent Number: 4,863,926
[45] Date of Patent: * Sep. 5, 1989

[54] NITRO ALIPHATIC COMPOUNDS, PROCESS FOR PREPARATION THEREOF AND USE THEREOF

[75] Inventors: Masanori Okamoto, Osaka; Morita Iwami, Takarazuka; Shigehiro Takase, Nishinomiya; Itsuo Uchida, Kyoto; Kazuyoshi Umehara, Ashiya; Masanobu Konsaka, Sakai; Hiroshi Imanaka, Osaka, all of Japan

[73] Assignee: Fujisawa Pharmaceutical Co., Ltd., Osaka, Japan

[*] Notice: The portion of the term of this patent subsequent to Aug. 30, 2005 has been disclaimed.

[21] Appl. No.: 119,091

[22] Filed: Nov. 10, 1987

Related U.S. Application Data

[62] Division of Ser. No. 786,754, Oct. 11, 1985, Pat. No. 4,778,804, which is a division of Ser. No. 559,260, Dec. 8, 1983, Pat. No. 4,767,768.

[30] Foreign Application Priority Data

Dec. 31, 1982 [GB] United Kingdom ................ 8237068

[51] Int. Cl.$^4$ ................ A61K 31/445; A61K 31/215; C07C 103/34; C07C 103/36

[52] U.S. Cl. .................... 514/255; 514/315; 514/330; 514/508; 514/534; 514/538; 514/543; 514/551; 514/563; 514/564; 514/561; 514/510; 514/619; 514/626; 514/640; 514/645; 564/166; 564/196; 564/197; 564/198; 560/21; 560/22; 560/156

[58] Field of Search ............... 514/315, 255, 330, 508, 514/534, 538, 549, 551, 563, 564, 561, 510, 619, 626, 640, 645; 564/166, 196, 197, 198; 560/21, 22, 156, 437, 560; 562/424, 435, 192, 225, 560, 437; 546/192, 225, 229, 232, 236, 237, 238, 245; 544/386, 398

[56] References Cited

U.S. PATENT DOCUMENTS

| | | | |
|---|---|---|---|
| 3,732,303 | 5/1973 | Fuhrmann et al. | 564/198 X |
| 3,746,757 | 7/1973 | Kikumoto | 564/198 X |
| 3,746,763 | 7/1973 | Fuhrmann et al. | 564/198 |
| 3,803,231 | 4/1974 | Fuhrmann et al. | 564/198 X |
| 3,849,476 | 11/1974 | Kikumoto | 564/198 X |
| 3,849,481 | 11/1974 | Fuhrmann et al. | 564/198 X |
| 3,873,301 | 3/1975 | O'Brien | 564/198 X |

Primary Examiner—Paul F. Shaver
Attorney, Agent, or Firm—Oblon, Spivak, McClelland, Maier & Neustadt

[57] ABSTRACT

New nitro aliphatic compounds useful as antithrombotic and antihypertensing agents are disclosed.

12 Claims, No Drawings

NITRO ALIPHATIC COMPOUNDS, PROCESS FOR PREPARATION THEREOF AND USE THEREOF

This is a division of application Ser. No. 06/786,754, filed Oct. 11, 1985, now U.S. Pat. No. 4,778,804, which in turn is a divisional of Ser. No. 06/559,260 now U.S. Pat. No. 4,767,768, filed Dec. 8, 1983.

This invention relates to new nitro aliphatic compounds. More particularly, this invention relates to new nitro aliphatic compounds and their pharmaceutically acceptable salts, which have antithrombotic and antihypertensive activity, to processes for preparation thereof, to a pharmaceutical composition comprising the same and to a method of use thereof.

New nitro aliphatic compounds of this invention are represented by the following formula (I):

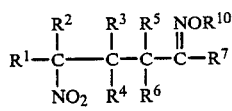

wherein
$R^1$ is hydrogen, lower alkyl or lower alkoxy-phenyl,
$R^2$ is hydrogen or lower alkyl,
$R^3$ and $R^5$ are each hydrogen, or together to form a bond for getting a group of the formula:

wherein $R^4$ and $R^6$ are each as defined below,
$R^4$ is lower alkyl,
$R^6$ is hydrogen or lower alkyl,
$R^7$ is hydrogen, hydroxyiminomethyl, cyano, formylpiperazinecarbonyl, alkanoyl, esterified carboxy, lower alkyl which may have hydroxy or lower alkanoyloxy, or a group of the formula:

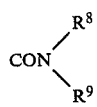

wherein $R^8$ and $R^9$ are each hydrogen, lower alkyl which may have one or more substituents selected from carboxy, esterified carboxy, hydroxy and phenyl, or $R^8$ and $R^9$ are together to form piperidine ring, and $R^{10}$ is hydrogen or lower alkyl which may have carboxy or esterified carboxy.

Particulars of the various definitions, which are mentioned hereinabove and hereinafter, and preferred examples thereof are explained in the following.

The term "lower" is intended to mean a group having 1 to 6 carbon atoms, unless otherwise provided.

(1) Re. Lower alkyl for $R^1$, $R^2$, $R^4$, $R^6$, $R^7$, $R_a^7$, $R^8$, $R^9$, $R^{10}$, $R_a^{10}$, $R_b^{10}$ and $R_c^{10}$:

Preferred examples of lower alkyl may include methyl, ethyl, propyl, butyl, pentyl, isopropyl, isobutyl, tert-butyl and the like.

(2) Re. Lower alkoxy moiety of lower alkoxyphenyl for $R^1$:

Preferred examples of lower alkoxy may include methoxy, ethoxy, propoxy, butoxy, tert-butoxy and the like.

(3) Re. Alkanoyl for $R^7$ and $R_a^7$:

Preferred examples of alkanoyl may include formyl, acetyl, propionyl, butyryl, iso-butyryl, tert-butyryl, valeryl, pivaloyl, lauroyl, stearoyl and the like.

(4) Re. Esterified carboxy for $R^7$ and $R_a^7$, and esterified carboxy moiety for $R^8$, $R^9$, $R^{10}$, $R_a^{10}$ and $R_b^{10}$:

Preferred examples of esterified carboxy may include alkyl ester, i.e. alkoxycarbonyl such as lower alkoxycarbonyl (e.g. methoxycarbonyl, ethoxycarbonyl, propoxycarbonyl, isopropoxycarbonyl, butoxycarbonyl, tert-butoxycarbonyl, etc.) and the like.

(5) Re. Lower alkanoyloxy moiety for $R^7$ and $R_a^7$:

Preferred examples of lower alkanoyloxy may include acetoxy, propionyloxy, butyryloxy, tert-butyryloxy and the like.

A pharmaceutically acceptable salt of the compound (I) may include a salt with an inorganic or organic base such as an alkali metal salt (e.g. sodium salt, potassium salt, etc.), an alkaline earth metal salt (e.g. calcium salt, etc.), ammonium salt, an organic amine salts such as ethanolamine salt, triethylamine salt, dicyclohexylamine salt and the like.

The compound (I) and its pharmaceutically acceptable salts of this invention can be prepared by various methods, which are explained as follows:

(1) Process 1:

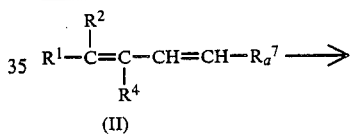

(II)

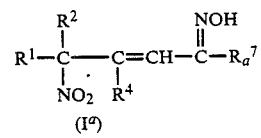

($I^a$)

(2) Process 2:

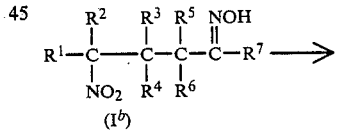

($I^b$)

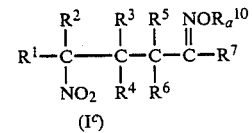

($I^c$)

(3) Process 3:

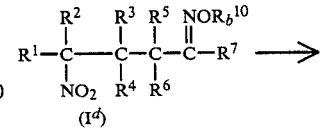

($I^d$)

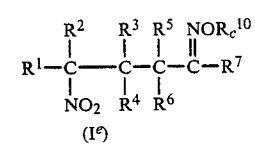

($I^e$)

(4) Process 4:

-continued

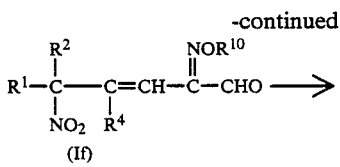
(If)

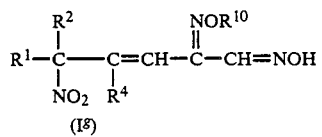
(Ig)

(5) Process 5:

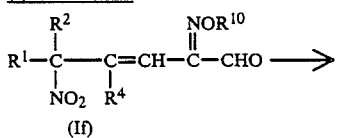
(If)

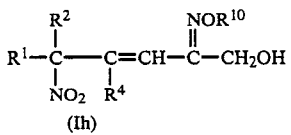
(Ih)

(6) Process 6:

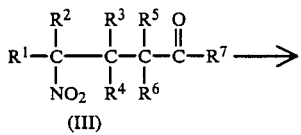
(III)

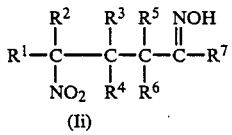
(Ii)

In the above formulae, $R_a^7$ is cyano, formylpiperazinecarbonyl, alkanoyl, esterified carboxy, lower alkyl which may have hydroxy or lower alkanoyloxy, or a group of the formula:

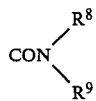

wherein $R^8$ and $R^9$ are each hydrogen, lower alkyl which may have one or more substituents selected from carboxy, esterified carboxy, hydroxy and phenyl, or $R^8$ and $R^9$ are together to form piperidine ring, $R_a^{10}$ is lower alkyl which may have carboxy or esterified carboxy, $R_b^{10}$ is lower alkyl having esterified carboxy, $R_c^{10}$ is lower alkyl having carboxy and $R^1$, $R^2$, $R^3$, $R^4$, $R^5$, $R^6$ and $R^7$ are each as defined above.

(1) Process 1: Compound (II)→Compound (I$^a$)

The compound (I$^a$) and its salt can be prepared by reacting the compound (II) or its salt with dinitrogen trioxide.

Preferred examples of salts of those compounds (II) and (I$^a$) may include the same ones as those of the compound (I).

This reaction is carried out by reacting directly the compound (II) or its salt with dinitrogen trioxide. The dinitrogen trioxide is usually prepared by nitrous acid or its salt and an acid, and accordingly this reaction is usually carried out by reacting the compound (II) or its salt with nitrous acid or its salt in the presence of an acid, instead that such dinitrogen trioxide is directly employed.

Preferred examples of salts of nitrous acid may include an alkali metal salt such as sodium salt, potassium salt and the like, an alkaline earth metal salt such as calcium salt, and the like.

Preferred examples of acids may include an inorganic or organic acid such as hydrochloric acid, sulfuric acid, formic acid, acetic acid and the like.

This reaction is preferably carried out in a solvent such as water, alcohol (e.g., methanol, ethanol, propanol, etc.), tetrahydrofuran, dioxane, dichloromethane or a mixture thereof.

This reaction is preferably carried out under somewhat milder conditions such as under cooling, at room temperature or under warming.

(2) Process 2: Compound (I$^b$)→Compound (I$^c$)

The compound (I$^c$) and its salt can be prepared by reacting the compound (I$^b$) or its salt with an alkylating agent.

Preferred examples of salts of those compounds (I$^c$) and (I$^b$) may include the same ones as those of the compound (I).

Preferred examples of an alkylating agent may include a diazo(lower)alkane (e.g. diazomethan, diazoethane, etc.), an alkoxycarbonyl-alkylhalide (e.g., tert-butoxy carbonylmethyl bromide, methoxycarbonylmethylchloride, etc.), carboxy-alkylhalide (e.g. carboxymethylbromide, carboxy-methylchloride, etc.), and the like.

This reaction is preferably carried out in a solvent such as an alcohol (e.g. methanol, ethanol, etc.), N,N-dimethylformamide, water or a mixture thereof.

This reaction is usually carried out under cooling or at room temperature.

(3) Process 3: Compound (I$^d$)→Compound (I$^e$)

The compound (I$^e$) and its salt can be prepared by subjecting the compound (I$^d$) or its salt to de-esterification reaction.

Preferred examples of salts of those compounds (I$^e$) and (I$^d$) may include the same ones as those of the compound (I).

The de-esterification reaction is carried out by a conventional method such as hydrolysis, reduction or the like, details of which are explained in the following:

(1) Hydrolysis:

Hydrolysis is preferably carried out in the presence of an acid or base.

Suitable acid includes an inorganic acid (e.g. hydrochloric acid, hydrobromic acid, sulfuric acid, etc.), an organic acid (e.g. formic acid, acetic acid, trifloroacetic acid, propionic acid, benzenesulfonic acid, p-toluenesulfonic acid, etc.), and the like.

Suitable base includes an inorganic base such as alkali or alkaline earth metal hydroxide or the corresponding carbonate or bicarbonate (e.g. sodium hydroxide, potassium hydroxide, sodium carbonate, potassium carbonate, sodium bicarbonate, calcium hydroxide, etc.), ammonium hydroxide or the like; an organic base such as an alkoxide or phenoxide of the above metal (e.g. sodium ethoxide, sodium methoxide, etc.), an amine such as mono-, di or tri-alkylamine (e.g. methylamine, ethylamine, N,N-dimethyl-1,3-propanediamine, trimethylamine, triethylamine, etc.) or the like.

The hydrolysis is preferably conducted under somewhat milder conditions such as under cooling or under warming in a solvent which does not have adverse influence to the reaction, e.g. water, a hydrophilic solvent such as alcohol (e.g. methanol, ethanol, propanol, etc.), acetone, N,N-dimethylformamide, etc. A liquid abovementioned acid and base can also be used as a solvent.

(2) Reduction:

Reduction, including chemical reduction and catalytic reduction, is carried out in a conventional manner.

Suitable reducing agents to be used in chemical reduction are a metal (e.g. tin, zinc, iron, etc.), or a combination of such metal and/or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, etc.).

Suitable catalysts to be used in catalytic reduction are conventional ones such as platinum catalysts (e.g. platinum plate, spongy platinum platinum black, colloidal platinum, platinum oxide, etc.), palladium catalysts (e.g. spongy palladium, palladium black, palladium oxide, palladium on carbon, colloidal palladium, etc.), or the like.

The reduction is usually carried out in a solvent such as water, an alcohol (e.g. methanol, ethanol, etc.) or the like.

The reduction is preferably carried out under somewhat milder conditions such as under cooling, at room temperature or under warming.

(4) Process 4: Compound ($I^f$)→Compound ($I^g$)

The compound ($I^g$) and its salt can be prepared by reacting the compound ($I^f$) or its salt with hydroxylamine or its acid addition salt.

Preferred examples of salts of those compounds ($I^f$) and ($I^g$) may include the same ones as those of the compound (I).

Preferred examples of acid addition salts of hydroxylamine may include ones with an organic or inorganic acid such as methane sulfonate, p-toluene sulfonate, hydrochloride, sulfate, nitrate, phosphate and the like.

The reaction is usually carried out in a solvent such as an alcohol (e.g. methanol, ethanol, etc.), chloroform, tetrahydrofuran, dichloromethane or a mixture thereof.

This reaction is preferably carried out under somewhat milder conditions such as under cooling or at room temperature.

(5) Process 5: Compound ($I^f$)→Compound ($I^h$)

The compound ($I^h$) and its salt can be prepared by reducing the compound ($I^f$) or its salt.

Preferred examples of salts of the compound ($I^h$) may include the same ones as those of the compound (I).

The reduction is carried out by a conventional method such as a catalytic reduction and a chemical reduction.

Preferred examples of catalysts to be used for a catalytic reduction may include the same ones as those illustrated for the catalyst in the aforementioned Process 3.

Preferred examples of a reducing agent to be used for a chemical reduction may include an alkali borohydride such as sodium borohydride, potassium borohydride and the like in addition to one illustrated for the chemical reduction in the aforementioned Process 3.

The reaction conditions for the reduction (i.e. reaction solvent, reaction temperature, etc.) may optionally be selected in accordance with the reduction method to be used. In general, it is preferable to employ a solvent such as water, an alcohol (e.g. methanol, ethanol, etc.) or a mixture thereof.

The reaction is preferably carried out under somewhat milder conditions such as under cooling or at room temperature.

(6) Process 6: Compound (III)→Compound (Ii)

The compound (Ii) and its salt can be prepared by reacting the compound (III) or its salt with hydroxylamine or its salt.

Preferred examples of salts of the compound (Ii) may include the same ones as those of the compound (I).

This reaction is carried out in the substantially same manner as that of the aforementioned Process 4.

The starting compounds (II) and (III) to be used in this invention are the new ones and some of them can be prepared by a method as follows and Preparations as described below, and the other compounds can be prepared by the substantially same methods as these methods.

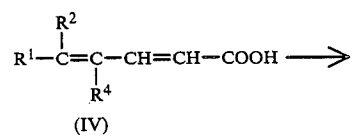

(IV)

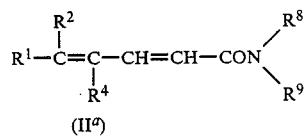

(II$^a$)

In the above formulae, $R^1$, $R^2$, $R^4$, $R^8$ and $R^9$ are each as defined above.

The compound (II$^a$) or its salt can be prepared by reacting the compound (IV) or its salt with an amine compound of the formula:

(wherein $R^8$ and $R^9$ are each as defined above) or its salt.

Preferred examples of salt of the compound (II$^a$) may include the same ones as those of the compound (I).

Preferred examples of salts of the amine compound may include the same ones as those illustrated for the acid addition salt of hydroxylamine in the aforementioned Process 4.

The reaction is preferably carried out as the first step by activating the carboxy group of the compound (IV) in a conventional manner, for example, in a form of its activated ester, acid halide, acid anhydride, a mixed anhydride, etc., and then reacting the resulting compound with the amine compound

or its salt.

In case that the amine compound is used in the form of salt, this reaction is preferably carried out in the presence of a base. Preferred examples of such a base may include the same ones as those illustrated for the base in the aforementioned Process 3.

This reaction is usually carried out in a solvent such as tetrahydrofuran, dichloromethane, dioxane, water or a mixture thereof.

The reaction is preferably carried out under somewhat milder conditions such as under cooling or at room temperature.

As to the nitro-aliphatic compounds (I) and starting compounds (II) and (III), it is to be noted that each of said compounds includes one or more stereo isomers and all of such isomers are included within the scope of this invention.

The new nitro aliphatic compounds (I) and their pharmaceutically acceptable salts of this invention have been found to possess relaxation effect on smooth-muscles (e.g. cardiovascular dilating effect, etc.) and hypotensive effect, and further are capable of inhibiting platelet aggregation.

Accordingly, the new nitro aliphatic compounds (I) and their pharmaceutically acceptable salts are useful for vasodilator which is used for the treatment of coronary insufficiency, angina pectoris and myocardial infarction, and also useful for anti-hypertensive agent which is used for the treatment of hypertension. Furthermore, they are used as an anti-thrombotic agent for the treatment of cerebral apoplexy, thrombosis and pulmonary embolism.

For the purpose of showing such pharmaceutical activities of the new nitro aliphatic compounds (I), pharmacological test data thereof are illustrated in the followings.

(i) Anti-platelet aggregation activity:

Inhibitory activity of the nitro aliphatic compounds of this invention against rabbit platelet aggregation was measured according to the method described below.

Platelet aggregation:

Blood was collected from the central ear arteries of male Japanese White rabbit (2.5 to 3.0 kg body weight). The blood was prevented from coagulation with 1 volume of 3.8% sodium citrate to 9 volumes of blood. Platelet rich plasma (PRP) was prepared by centrifugation of the blood at 1300 rpm for 10 min. at 10° C. The PRP was diluted with platelet poor plasma obtained by further centrifugation of the blood at 3000 rpm for 10 min. The platelet counts in the PRP used for aggregation studies were about $4.0 \times 10^5$ platelets/mm$^3$. Aggregometry was performed with platelet aggregating agents in a SIENCO dual sample aggregometer (DP-247 E) at 37° C., using 0.3 ml combined volume of PRP and reagents in a cylindrical glass cuvette under constant stirring with a magnetic stirring bar. Platelet aggregation was measured turbidimetrically by recording changes in the light transmission of PRP during aggregation. Activities of inhibitors were expressed as $IC_{50}$ values i.e. concentrations required to inhibit the platelet aggregation responses by 50%. Collagen was used in amounts (2 to 20 μg/ml for PRP) sufficient to induce a response that was 80 to 90% of the maximum obtainable. Arachidonic acid was used at a final concentration of 5 μM. Similarly a final concentration of adenosine di-phosphate (ADP), usually 1 to 5 μM was choosen to induce approximately 75% of the maximum aggregation. Thrombin was used at a final concentration of 0.3 U/ml.

Results are shown in the following Tables 1 and 2.

TABLE 1

| Inducers | $IC_{50}$ value (μg/ml) Test Compound (Example 1) |
|---|---|
| Collagen | 0.07 |
| Thrombin | 0.15 |
| ADP | 0.15 |
| Arachidonic acid | 0.75 |

TABLE 2

| Test Compound (Example Number) | $IC_{50}$ (μg/ml) (Inducer:Thrombin) |
|---|---|
| Example 2 | 0.15 |
| Example 3 | 0.3 |
| Example 4 | 0.3 |
| Example 6 | 0.15 |
| Example 7 | 0.75 |
| Example 10 | 0.3 |
| Example 11 | 0.15 |
| Example 14 | 0.30 |
| Example 15 | 0.75 |
| Example 17 | 1.5 |
| Example 18 | 3.0 |
| Example 19 | 0.07 |
| Example 20 | 0.15 |
| Example 21 | 0.15 |
| Example 22 | 0.75 |
| Example 23 | 0.15 |
| Example 24 | 1.5 |
| Example 25 | 6.0 |
| Example 28 | 6.0 |

(ii) Vasodilating activity in vitro:

The vasodilating activity of the nitro-aliphatic compound (I) was measured by the superfusion technique. The method is as follows:

Male Sprague-Dawly rats of 8–10 weeks age were killed by a blow on the head and the throracic aorta was quickly removed. After removing fatty tissues, spiral strips (2 mm width and 50 mm length) were made from the aorta and were suspended under a resting tension of 1 gram in 30 ml organ baths containing warm (37° C.) oxygenated (95% $O_2$:5% $CO_2$) Tyrode solution of the following composition: NaCl 137 mM (8 g/liter), KCl 2.7 mM (0.2 g/liter), $CaCl_2 2H_2O$ 1.8 mM (0.264 g/liter), $MgCl_2 6H_2O$ 1.02 mM (0.208 g/liter), $NaHCO_3$ 11.9 mM (1 g/liter), $NaH_2PO_4 2H_2O$ 0.42 mM (0.066 g/liter) and glucose 5.55 mM (1 g/liter).

The tissues were equilibrated for almost 90 minutes and then were superfused with Tyrode solution (10 ml/min) and noradrenaline-saline solution (0.6 μg/ml) (0.5 ml/min.) which increases the tension of the tissues by about 500 mg. Changes of tension of the tissues were measured isometrically by means of force displacement transducers coupled to a polygraph. The vasodilating activity is expressed as the dose of each compound producing fifty percent reduction of the tension of the tissues ($ED_{50}$).

Results are shown in the following Table 3.

TABLE 3

| Test Compound (Example Number) | Relaxation of aorta $ED_{50}$ (μg) |
|---|---|
| Example 1 | 0.05 |
| Example 2 | 0.20 |
| Example 3 | 0.10 |
| Example 4 | 0.10 |
| Example 6 | 2.0 |
| Example 7 | 0.5 |
| Example 10 | 5 |
| Example 11 | 0.1 |
| Example 12 | 0.05 |

TABLE 3-continued

| Test Compound (Example Number) | Relaxation of aorta ED$_{50}$ ($\mu$g) |
| --- | --- |
| Example 13 | 0.25 |
| Example 14 | 0.05 |
| Example 15 | 2.5 |
| Example 17 | 0.25 |
| Example 18 | 0.025 |
| Example 19 | 0.01 |
| Example 20 | 0.1 |
| Example 21 | 0.05 |
| Example 22 | 0.25 |
| Example 23 | 0.025 |
| Example 25 | 5 |
| Example 26 | 5 |
| Example 27 | 0.25 |
| Example 28 | 0.5 |

(iii) Hypotensive activity in experimental animal:

A 8 weeks-old Sprague-Dowley strain rat was anesthetized with urethane (0.7 g/kg, i.p). Blood pressure was recorded from femoral artery using a transducer coupled to a Biophysiograph 180 system (made by Sanei Sokuki Co., Ltd.). The femoral vein was cannulated to permit intravenous injection of the test compound. The test compound was dissolved in saline and injected in a volume of 0.2 ml. The results are shown in the following Table 4.

TABLE 4

| Test Compound (Example number) | Hypotensive effect | |
| --- | --- | --- |
| | Maximal decrease (mm Hg) | Duration (min) |
| Example 100 $\mu$g/kg | 40 | 4 |
| 1 10 $\mu$g/kg | 10 | 1.5 |

The pharmaceutical composition of this invention can be used in the form of a pharmaceutical preparation, for example, in solid, semisolid or liquid form, which contains an active substance of this invention in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The pharmaceutical compositions can also contain preservative or bacteriostatic agents to keep the active ingredient in the desired preparations stable in activity. The active object compound is included in the pharmaceutical composition in an amount sufficient to produce the desired therapeutic effect upon the process or condition of diseases.

For applying this composition to humans, it is preferable to apply it by intravenous, intramuscular or oral administration. While the dosage or therapeutically effective amount of the object compound of this invention varies from and also depends upon the age and condition of each individual patient to be treated, a daily dose of about 0.1-100 mg of the active ingredient/kg of a human being or an animal is generally given for treating diseases, and an average single dose of about 10 mg, 50 mg, 100 mg, 250 mg, and 500 mg is generally administered.

The following examples are given for purpose of illustrating this invention.

PREPARATION 1

Triethyl phosphonoacetate (448 g) was added dropwise to sodium hydride (88 g, 60%) in anhydrous benzene (2 l) at 0° C. with stirring under dry nitrogen atomosphere. After the mixture was stirred at room temperature for 30 minutes, (E)-2-ethyl-2-butenal (196 g) was added thereto slowly at 0° C. The resulting mixture was allowed to stand at room temperature for 30 minutes, diluted with water (2 l) and then extracted with two portions of ethyl acetate (1 l×2). The combined extracts were washed successively with water and brine, and then dried over magnesium sulfate. Removal of the solvent gave an oil which was purified by distillation under reduced pressure to give ethyl (E,E)-4-ethyl-2,4-hexadienoate (290 g).

NMR: $\delta$ (CDCl$_3$) 7.2 (1H, d, J=16 Hz), 6.07–5.67 (2H, m), 4.2 (2H, q, J=7 Hz), 2.26 (2H, q, J=7 Hz), 1.78 (3H, d, J=7 Hz), 1.27 (3H, t, J=7 Hz), 0.97 (3H, t, J=7 Hz).

IR: $\nu_{Max}^{CHCl_3}$ 2960, 2930, 2870, 1690, 1620, 1470, 1450, 1390, 1370, 1310, 1275, 1265, 1250, 1180, 1100, 1080, 1060, 1040, 980, 940, 870, 820 cm$^{-1}$.

PREPARATION 2

Ethyl (E,E)-4-ethyl-2,4-hexadienoate (134 g) was dissolved in methanol (200 ml) and 1N aqueous sodium hydroxide (880 ml) was added to the solution. The resulting mixture was stirred at room temperature for 20 hours under nitrogen atmosphere. After removal of methanol, the residual aqueous solution was washed with ether. The aqueous layer was acidified with conc. hydrochloric acid and then extracted with three portions of ethyl acetate (500 ml33 3). The combined extracts were washed with brine, dried over magnesium sulfate and then evaporated to dryness to give a white powder which was crystallized from ether to give (E,E)-4-ethyl-2,4-hexadienoic acid (108 g).

mp: 79°–81° C.

NMR: $\delta$ (CDCl$_3$) 11.2 (1H, broad s), 7.33 (1H, d, J=16 Hz), 6.00 (1H, q, J=7 Hz), 5.80 (1H, d, J=16 Hz), 2.29 (2H, q, J=7 Hz), 1.83 (3H, d, J=7 Hz), 1.0 (3H, t, J=7 Hz).

IR: $\nu_{Max}^{CHCl_3}$ 2970, 2930, 2880, 2700, 2600, 1680, 1620, 1470, 1460, 1420, 1380, 1310, 1290, 1270, 1200, 1130, 1080, 1060, 990, 960, 940, 870, 820 cm$^{-1}$.

PREPARATION 3

(E,E)-4-Ethyl-2,4-hexadienoic acid (108 g) was dissolved in tetrahydrofuran (2 l) and triethylamine (108 ml) was added to the solution. The mixture was stirred at room temperature for 30 minutes and then ethyl chloroformate (74 ml) was added dropwise thereto at −20° C. with stirring. The resulting mixture was stirred at the same temperature for 60 minutes, and then dry ammonia gas was bubbled into the reaction mixture at −20° C. for until the mixture was saturated with ammonia. The mixture was stirred at the same temperature for 60 minutes and then concentrated. The resulting concentrate was diluted with water and then extracted with two portions of ethyl acetate (500 ml×2). The combined extracts were washed successively with an aqueous sodium carbonate and brine, dried over magnesium sulfate and then evaporated to dryness to give a pale yellow oil (79 g). The oil was crystallized from ether to give (E,E)-4-ethyl-2,4-hexadienamide (34 g) as colorless crystals.

mp: 57°–58° C.

NMR: δδ(CDCl$_3$) 7.13 (1H, d, J=16 Hz), 6.2–5.7 (4H, m), 2.27 (2H, q, J=7 Hz), 1.78 (3H, d, J=7 Hz), 1.0 (3H, t, J=7 Hz).

IR: $\nu_{Max}^{CHCl_3}$ 3550, 3500, 3430, 3350, 3200, 3020, 3000, 2950, 2900, 1670, 1620, 1590, 1460, 1400, 1380, 1310, 1280, 1240–1220, 1100, 1080, 1060, 990, 970, 860, 820 cm$^{-1}$.

PREPARATION 4

(E,E)-4-Ethyl-2,4-hexadienoic acid (5 g) was dissolved in tetrahydrofuran (300 ml) and triethylamine (5 ml) was added to the solution. The mixture was stirred at room temperature for 30 minutes and then ethyl chloroformate (3.4 ml) was added dropwise thereto at −20° C. with stirring. The resulting mixture was stirred at the same temperature for 60 minutes.

n-Butylamine (3.6 ml) was added to the reaction mixture at −20° C. The resulting mixture was stirred at the same temperature for 60 minutes. The reaction mixture was concentrated and the concentrate was diluted with water, and then extracted with two portions of ethyl acetate (100 ml×2). The combined extracts were washed with successively an aqueous sodium carbonate solution and brine, dried over magnesium sulfate and then evaporated to dryness to give an oil (6.5 g) which was subjected to column chromatography on silicagel, eluting with chloroform containing 2% methanol, to give (E,E)-N-n-butyl-4-ethyl-2,4-hexadienamide (5.8 g).

NMR: δ (CDCl$_3$) 7.05 (1H, d, J=16 Hz), 6.33 (1H, broad s), 5.75 (1H, q, J=7 Hz), 5.7 (1H, d, J=16 Hz), 3.4–3.1 (2H, m), 2.22 (2H, q, J=7 Hz), 1.77 (3H, d, J=7 Hz), 1.7–1.2 (4H, m), 1.1–0.8 (6H, m).

IR: $\nu_{Max}^{CHCl_3}$ 3450, 3300, 2960, 2930, 2870, 1660, 1610, 1510, 1470, 1450, 1440, 1320, 1300, 1260, 1200, 980, 820 cm$^{-1}$.

PREPARATION 5

(E,E)-N-Methyl-4-ethyl-2,4-hexadienamide (2 g) was prepared in substantially the same manner as that of Preparation 4 from (E,E)-4-ethyl-2,4-hexadienoic acid (5 g) and methylamine (40% in water, 11 ml).

NMR: δ (CDCl$_3$) 7.13 (1H, d, J=16 Hz), 7.0 (1H, m), 5.9 (1H, d, J=16 Hz), 5.87 (1H, q, J=7 Hz), 2.85 (3H, d, J=5 Hz), 2.22 (2H, q, J=7 Hz), 1.75 (3H, d, J=7 Hz), 0.95 (3H, t, J=7 Hz).

IR: $\nu_{Max}^{CHCl_3}$ 3440, 3270, 2950, 2900, 2850, 1640, 1600, 1520, 1410, 1320, 1260, 1050, 980, 820 cm$^{-1}$.

PREPARATION 6

1-Formyl-4-[(E,E)-4-ethyl-2,4-hexadienoyl]piperazine (6.8 g) was prepared in substantially the same manner as that of Preparation 4 from (E,E)-4-ethyl-2,4-hexadienoic acid (5 g) and 1-piperazinecarbaldehyde (7.4 ml).

NMR: δ (CDCl$_3$) 8.08 (1H, s), 7.23 (1H, d, J=16 Hz), 6.17 (1H, d, J=16 Hz), 5.92 (1H, q, J=7 Hz), 3.7–3.3 (8H, m), 2.28 (2H, q, J=7 Hz), 1.78 (3H, d, J=7 Hz), 1.0 (3H, t, J=7 Hz).

IR: $\nu_{Max}^{CHCl_3}$ 2970, 2950, 2900, 2850, 1660, 1630, 1610, 1590, 1450, 1420, 1390, 1290, 1270, 1260, 1230, 1000 cm$^{-1}$.

PREPARATION 7

To a solution of (E,E)-4-ethyl-2,4-hexadienoic acid (2.8 g) and N-hydroxysuccinimide (2.3 g) in dioxane (20 ml) was added dicyclohexylcarbodiimide (4.32 g). The mixture was stirred at ambient temperature overnight and then filtered. The filtrate was concentrated to dryness under reduced pressure to give a residue which was dissolved in tetrahydrofuran (100 ml). To the solution was added a solution of glycine (4.5 g) and triethylamine (8.34 ml) in water (60 ml). The resulting mixture was stirred at ambient temperature for 5 hours, acidified with 1N hydrochloric acid and then extracted with ethyl acetate. The extract was washed with water, dried over magnesium sulfate, and then concentrated to dryness under reduced pressure to give a crystalline residue. The residue was triturated with a mixture of chloroform and hexane to give N-[(E,E)-4-ethyl-2,4-hexadienoyl]glycine (1.72 g).

IR (Nujol): 3300, 1720, 1640, 1580 cm$^{-1}$.

PREPARATION 8

N-[(E,E)-4-Ethyl-2,4-hexadienoyl]piperidine (1.8 g) was prepared in substantially the same manner as that of Preparation 7 from (E,E)-4-ethyl-2,4-hexadienoic acid (1.4 g) and piperidine (10 ml).

IR: $\nu_{Max}^{CHCl_3}$ 3250, 1685, 1640, 1600 cm$^{-1}$.

PREPARATION 9

To a solution of (E,E)-4-ethyl-2,4-hexadienoic acid (7 g) and N-hydroxysuccinimide (5.75 g) in dioxane (100 ml) was added dicyclohexylcarbodiimide (10.8 g). The mixture was stirred at ambient temperature overnight and then filtered. The filtrate was concentrated under reduced pressure to give a residue which was recrystallized from a mixture of ether and petroleum ether to give N-[(E,E)-4-ethyl-2,4-hexadienoyloxy]succinimide (10.73 g).

NMR: δ (CDCl$_3$) 7.45 (1H, d, J=16 Hz), 6.1 (1H, q, J=7 Hz), 5.9 (1H, d, J=16 Hz), 2.8 (4H, s), 2.3 (2H, q, J=7 Hz), 1.83 (3H, d, J=7 Hz), 1.0 (3H, t, J=7 Hz).

PREPARATION 10

To a solution of N-[(E,E)-4-ethyl-2,4-hexadienoyloxy]succinimide (1.19 g) in a mixture of tetrahydrofuran (50 ml) and dimethylformamide (30 ml) was added a solution of L-threonine (2.38 g) and triethylamine (2.78 ml) in water (50 ml). The mixture was stirred at ambient temperature for 6 hours and then acidified with 1N hydrochloric acid. The resulting mixture was extracted with ethyl acetate, washed with water and then dried over magnesium sulfate. The solvent was distilled off under reduced pressure to give N-[(E,E)-4-ethyl-2,4-hexadienoyl]-L-threonine (640 mg).

IR: $\nu_{Max}^{CHCl_3}$ 3400, 3300, 2950, 2900, 1715, 1650, 1600, 1500 cm$^{-1}$.

PREPARATION 11

(E,E)-N-Benzyl-4-ethyl-2,4-hexadienamide (1 g) was prepared in substantially the same manner as that of Preparation 10 from N-[(E,E)-4-ethyl-2,4-hexadienoyloxy]succinimide (1.19 g) and benzylamine (1 ml).

IR: $\nu_{Max}^{CHCl_3}$ 3400, 1650, 1605, 1500 cm$^{-1}$.

PREPARATION 12

Methyl 2-[(E,E)-4-ethyl-2,4-hexadienoylamino]acetate (11.5 g) was prepared in the substantially same manner as that of Preparation 4 from (E,E)-4-ethyl-2,4-hexadienoic acid (10 g) and glycine methyl ester (12.8 g).

NMR: δ (CDCl$_3$) 7.2 (1H, d, J=16 Hz), 6.33 (1H, broad s), 5.9 (1H, q, J=7 Hz), 5.87 (1H, d, J=16 Hz), 4.15 (2H, d, J=6 Hz), 3.77 (3H, s), 2.27 (2H, q, J=7 Hz), 1.8 (3H, d, J=7 Hz), 1.0 (3H, t, J=7 Hz).

IR: $\nu_{Max}^{CHCl_3}$ 3430, 3000, 1740, 1660, 1610, 1510, 1440, 1380 cm$^{-1}$.

PREPARATION 13

To a mixture of sodium hydride (60% in oil, 7.5 g) and dry benzene (200 ml) was added dropwise diethyl cyanomethylphosphonate (30 g) with stirring at 0° C. under dry nitrogen atmosphere. After stirring for 60 minutes at room temperature, a solution of (E)-2-ethyl-2-butenal (16.6 g) in dry benzene was added thereto at 0° C. with stirring. The resulting mixture was allowed to stand at room temperature for 60 minutes and diluted with water and then extracted with ethyl acetate. The extract was washed successively with water and brine, and then dried over magnesium sulfate. Removal of the solvent gave an oil which was purified by distillation under reduced pressure to give (E,E)-4-ethyl-2,4-hexadienenitrile (8.4 g).

NMR: δ (CDCl$_3$) 6.97 (1H, d, J=16 Hz), 5.93 (1H, q, J=7 Hz), 5.27 (1H, d, J=16 Hz), 2.27 (2H, q, J=7 Hz), 1.83 (3H, d, J=7 Hz), 1.0 (3H, t, J=7 Hz).

IR: $\nu_{Max}^{CHCl_3}$ 3000, 2250, 1630, 1605, 1480, 1460, 1400, 1380, 1230, 975 cm$^{-1}$.

PREPARATION 14

To a suspension of lithium aluminum hydride (1.8 g) in dry ether (150 ml) was added dropwise a solution of ethyl (E,E)-4-ethyl-2,4-hexadienoate (10 g) in dry ether (10 ml) at 0° C.

The mixture was stirred at room temperature for 30 minutes and small amount of water was added thereto to decompose the excess lithium aluminum hydride, and then filtered. The filtrate was diluted with ethyl acetate, washed successively with water and brine, and then dried over magnesium sulfate. Removal of the solvent under reduced pressure gave an oil.

The oil was dissolved in chloroform (200 ml) and manganese dioxide (60 g) was added to the solution. The resulting mixture was stirred at room temperature for 24 hours and filtered. The filtrate was evaporated to dryness in vacuo to give (E,E)-4-ethyl-2,4-hexadienal (4.2 g).

NMR: δ (CDCl$_3$) 9.53 (1H, d, J=7 Hz), 7.03 (1H, d, J=16 Hz), 6.3–5.9 (2H, m), 2.3 (2H, q, J=7 Hz), 1.83 (3H, d, J=7 Hz), 1.0 (3H, q, J=7 Hz).

IR: $\nu_{Max}^{CHCl_3}$ 2980, 2730, 1670, 1625, 1140, 970 cm$^{-1}$.

PREPARATION 15

To a suspension of lithium aluminum hydride (0.18 g) in dry ether (20 ml) was added a solution of ethyl (E,E)-4-ethyl-2,4-hexadienoate (1 g) in ether (5 ml) at 0° C. The resulting mixture was stirred at room temperature for 15 minutes. Small amount of water was added to the reaction mixture. The resulting mixture was filtered and the filtrate was washed successively with water and brine. Removal of the solvent gave an oil.

To the residue were added pyridine (1 ml) and acetic anhydride (0.5 ml), and the mixture was allowed to stand at room temperature overnight.

The reaction mixture was poured into a cold 1N hydrochloric acid solution (50 ml) and extracted with ethyl acetate. The extract was washed successively with 5% aqueous sodium bicarbonate solution and brine, dried over magnesium sulfate, and then evaporated to dryness to give (E,E)-1-acetoxy-4-ethyl-2,4-hexadiene (0.48 g)

IR: $\nu_{Max}^{CHCl_3}$ 2980, 1720, 1640, 1460, 1380, 1240 cm$^{-1}$.

PREPARATION 16

To a solution of nitroethane (56 ml) and benzyltrimethylammonium hydroxide (40% in methanol, 7 ml) in dioxane (80 ml) was added methyl (E)-2-pentenoate (20 g) at 70° C. with stirring. The resulting mixture was stirred at 70° C. for 2 hours. After cooling, the reaction mixture was acidified with 1N hydrochloric acid, diluted with water, and then extracted with ether. The extract was washed successively with water and brine, dried over magnesium sulfate and then evaporated to dryness to give methyl 3-ethyl-4-nitro pentanoate (30 g).

NMR: δ (CDCl$_3$) 4.8 (1H, m), 3.75 (3H, s), 2.6–2.4 (3H, m), 1.8–1.3 (5H, m), 1.0 (3H, m).

IR: $\nu_{Max}^{CHCl_3}$ 2960, 1730, 1545, 1460, 1440, 1390, 1200, 1180 cm$^{-1}$.

PREPARATION 17

Diisobutyl aluminum hydride (25% in toluene, 39 ml) was added to a solution of methyl 3-ethyl-4-nitro pentanoate (8.5 g) in dry toluene (300 ml) at −70° C. with stirring under nitrogen atmosphere. The resulting mixture was stirred at −70° C. for an hour and 2N hydrochloric acid (40 ml) was added to the reaction mixture. The mixture was diluted with ethyl acetate and filtered. The filtrate was washed successively with water and brine, dried over magnesium sulfate, and then evaporated to dryness.

The resulting oil was dissolved in dichloromethane (100 ml) and pyridinium chlorochromate (14 g) was added to the solution. The resulting mixture was stirred at room temperature for an hour and diluted with 5 volumes of ether. The supernatant was obtained by decantation from the mixture and passed through a column of magnesium silicate. The passed solution was evaporated to dryness in vacuo to give 3-ethyl-4-nitropentanal (5 g).

NMR: δ (CDCl$_3$) 9.8 (1H, broad s), 4.9–4.5 (1H, m), 2.8–2.3 (3H, m), 1.7–1.3 (5H, m), 0.95 (3H, m).

IR: $\nu_{Max}^{CHCl_3}$ 2960, 2720, 1720, 1550, 1460, 1390, 1360 cm$^{-1}$.

PREPARATION 18

To a suspension of sodium cyanide (4.5 g) and 3-ethyl-4-nitro-pentanal (7.5 g) in ether (50 ml) was added conc. hydrochloric acid (7.5 ml) at 0° C. with stirring. The resulting mixture was stirred at 0° C. for an hour, diluted with ether, washed successively with water and brine, dried over magnesium sulfate, and then evaporated to dryness in vacuo to give 4-ethyl-2-hydroxy-5-nitro-hexanenitrile (8.1 g).

IR: $\nu_{Max}^{CHCl_3}$ 3600, 3400, 2960, 2250, 1550, 1460, 1390 cm$^{-1}$.

PREPARATION 19

A mixture of conc. hydrochloric acid (2.4 ml) and conc. sulfuric acid (0.38 ml) was added to a solution of 4-ethyl-2-hydroxy-5-nitrohexanenitrile (1 g) in ether (2 ml) at 0° C. with stirring. The resulting mixture was allowed to stand at room temperature overnight, diluted with cold water, and then extracted with ethyl acetate. The extract was washed with successively with water and 5% aqueous sodium bicarbonate, dried over magnesium sulfate and then evaporated to dryness in vacuo to give 4-ethyl-2-hydroxy-5-nitrohexanamide (0.46 g).

NMR: δ (CDCl$_3$) 6.8 (1H, broad s), 6.3 (1H, broad s), 4.75 (1H, m), 4.3–4.0 (2H, m), 2.4–2.1 (1H, m), 1.9–1.3 (7H, m), 0.95 (3H, m).

IR: $\nu_{Max}^{CHCl_3}$ 3550, 3500, 3400, 3000, 1680, 1550, 1400, 1100 cm$^{-1}$.

PREPARATION 20

N-[(E,E)-4-Ethyl-2,4-hexadienoyl]-4-aminobutyric acid (1 g) was prepared in the substantially same manner as that of the Preparation 10 from N-[(E,E)-4-ethyl-2,4-hexadienoyloxy]succinimide (1.19 g) and 4-aminobutyric acid (2 g).

NMR: δ (CDCl$_3$) 7.2 (1H, d, J=14 Hz), 6.3–5.7 (4H, m), 3.5 (2H, m), 2.7–2.0 (6H, m), 1.8 (3H, d, J=7 Hz), 1.0 (3H, t, J=7 Hz).

IR: $\nu_{Max}^{CHCl_3}$ 3400, 2800–2400, 1700, 1650, 1600, 1520 cm$^{-1}$.

PREPARATION 21

Triethylphosphonoacetate (11.52 g) was added dropwise to a suspension of sodium hydride (2.08 g, 60%) in benzene (80 ml) at 0° C. The mixture was stirred at room temperature for an hour and 2-ethyl-3-methyl-2-butenal (4.8 g) was added slowly thereto at 0° C. The resulting mixture was stirred at room temperature for 2 hours and then allowed to stand at the same temperature overnight. The reaction mixture was poured into water and extracted with ether. The extract was washed with water, dried over magnesium sulfate, and then concentrated to dryness under reduced pressure to give ethyl (E)-4-ethyl-5-methylhexa-2,4-dienoate (7.6 g).

NMR: δ (CDCl$_3$) 7.8 (1H, d, J=16 Hz), 5.8 (1H, d, J=16 Hz), 4.25 (2H, q, J=7 Hz), 2.3 (2H, q, J=7 Hz), 1.95 (3H, s), 1.88 (3H, s), 1.3 (3H, t, J=7 Hz), 1.0 (3H, t, J=7 Hz).

IR: $\nu_{max}^{CHCl_3}$ 2950, 1700, 1620 cm$^{-1}$.

PREPARATION 22

(E)-4-Ethyl-5-methyl-hexa-2,4-dienoic acid (2.5 g) was prepared in the substantially same manner as that of Preparation 2 from ethyl (E)-4-ethyl-5-methylhexa-2,4-dienoate (6 g).

NMR: δ (CDCl$_3$) 8.4 (1H, broad s), 7.9 (1H, d, J=16 Hz), 5.8 (1H, d, J=16 Hz), 2.3 (2H, q, J=7 Hz), 1.95 (3H, s), 1.85 (3H, s), 1.0 (3H, t, J=7 Hz).

IR: $\nu_{Max}^{CHCl_3}$ 3000, 3200–2400, 1690, 1615 cm$^{-1}$.

PREPARATION 23

(E)-4-Ethyl-5-methylhexa-2,4-dienamide (1.2 g) was prepared in the substantially same manner as that of Preparation 4 from (E)-4-ethyl-5-methyl-hexa-2,4-dienoic acid (2.34 g).

NMR: δ (CDCl$_3$) 7.7 (1H, d, J=16 Hz), 5.8 (1H, d, J=16 Hz), 5.7 (2H, broad s), 2.3 (2H, q, J=7 Hz), 1.9 (3H, s), 1.85 (3H, s), 1.0 (3H, t, J=7 Hz).

IR: $\nu_{Max}^{CHCl_3}$ 3550, 3450, 3000, 1720, 1670, 1615, 1590 cm$^{-1}$.

PREPARATION 24

To a suspension of sodium hydride (1.3 g, 60%) in anhydrous benzene (150 ml) was added dropwise triethyl phosphonoacetate (6.72 g) at 0° C. under nitrogen atmosphere. The mixture was stirred at room temperature for an hour and (E)-3-ethyl-3-penten-2-one (3.36 g) was added to the reaction mixture. The resulting mixture was stirred at 60° C. for 20 hours and diluted with water and then extracted with ethyl acetate. The extract was washed with brine and dried over magnesium sulfate. The solvent was removed under reduced pressure and the residue was chromatographed on a silica gel column and eluted with a mixture of hexane and chloroform (1:1).

The fractions containing the object compound were combined and the solvent was evaporated to dryness to give ethyl (E,E)-4-ethyl-3-methyl-2,4-hexadienoate (3.3 g).

NMR: δ (CDCl$_3$) 5.88 (1H, q, J=7 Hz), 5.73 (1H, s), 4.27 (2H, q, J=7 Hz), 2.37 (2H, q, J=7 Hz), 2.30 (3H, s), 1.76 (3H, d, J=7 Hz), 1.30 (3H, t, J=7 Hz), 0.97 (3H, t, J=7 Hz).

IR: $\nu_{Max}^{CHCl_3}$ 2960, 2930, 2870, 1690, 1620 cm$^{-1}$.

PREPARATION 25

(E,E)-4-Ethyl-3-methyl-2,4-hexadienoic acid (1.28 g) was prepared in the substantially same manner as that of Preparation 2 from ethyl (E,E)-4-ethyl-3-methyl-2,4-hexadienoate (1.82 g).

NMR: δ (CDCl$_3$) 9.70–8.70 (1H, broad s), 5.95 (1H, q, J=7 Hz), 5.90 (1H, s), 2.35 (2H, q, J=7 Hz), 2.30 (3H, s), 1.78 (3H, d, J=7 Hz), 1.06 (3H, t, J=7 Hz).

IR: $\nu_{Max}^{Nujol}$ 3100, 2830, 2700, 2600, 2400, 1695, 1610 cm$^{-1}$.

PREPARATION 26

(E,E)-4-Ethyl-3-methyl-2,4-hexadienamide (730 mg) was prepared in the substantially same manner as that of Preparation 4 from (E,E)-4-ethyl-3-methyl-2,4-hexadienoic acid (1.23 g) and 28% aqueous ammonia (10 ml).

NMR: δ (CDCl$_3$) 5.83 (1H, q, J=7 Hz), 5.80 (1H, s), 5.30–4.40 (2H, broad s), 2.32 (2H, q, J=7 Hz), 2.24 (3H, s), 1.74 (3H, d, J=7 Hz), 0.96 (3H, t, J=7 Hz).

IR: $\nu_{Max}^{CHCl_3}$ 3560, 3450, 3200, 3005, 2950, 2900, 1670, 1610, 1590 cm$^{-1}$.

PREPARATION 27

(E,E)-4-Methyl-2,4-hexadienamide (1.2 g) was prepared in the substantially same manner as that of Preparation 4 from (E,E)-4-methyl-2,4-hexadienoic acid (2.5 g) and 28% aqueous ammonia (10 ml).

NMR: δ (CDCl$_3$) 7.23 (1H, d, J=16 Hz), 5.93 (3H, m), 5.80 (1H, d, J=16 Hz), 1.73 (3H, s), 1.78 (3H, d, J=6 Hz).

IR: $\nu_{max}^{CHCl_3}$ 3550, 3430, 3000, 1670, 1620, 1590, 1380, 1340, 1070 cm$^{-1}$.

PREPARATION 28

(E)-4-Methyl-2,4-pentadienamide (1.2 g) was prepared in the substantially same manner as that of Preparation 4 from (E)-4-methyl-2,4-pentadienoic acid (2.3 g) and 28% aqueous ammonia (10 ml).

NMR: δ (CDCl$_3$) 7.28 (1H, d, J=15 Hz), 5.90 (1H, d, J=15 Hz), 6.10 (2H, m), 5.30 (2H, s), 1.87 (3H, s).

IR: $\nu_{Max}^{CHCl_3}$ 3500, 3420, 3350, 3200, 3000, 1675, 1630, 1610, 1590, 1380, 1340, 1220 cm$^{-1}$.

PREPARATION 29

Ethyl 2-((E)-4-methoxybenzylidene)butyrate (20 g) was prepared in the substantially same manner as that of Preparation 1 from ethyl 2-diethylphosphonobutyrate (25 g) and p-methoxybenzaldehyde (12 g).

NMR: $\delta$ (CDCl$_3$) 7.57 (1H, s), 7.33 (2H, d, J=9 Hz), 6.88 (2H, J=9 Hz), 4.27 (2H, q, J=7 Hz), 3.82 (3H, s), 2.58 (2H, q, J=7 Hz), 1.33 (3H, s), 1.17 (3H, s).

IR: $\nu_{Max}^{CHCl_3}$ 2960, 1695, 1605, 1240, 835 cm$^{-1}$.

PREPARATION 30

To a suspension of lithium aluminum hydride (3 g) in dry ether (300 ml) was added a solution of ethyl 2-((E)-4-methoxybenzylidene)butyrate (19 g) in dry ether (30 ml) at 0° C. with stirring. The mixture was stirred at the same temperature for 3 hours and excess lithium aluminum hydride was decomposed with wet ether. The reaction mixture was filtered and the filtrate was washed with water, dried over magnesium sulfate and then evaporated to dryness to give 2-((E)-4-methoxybenzylidene)butan-1-ol (13 g).

NMR: $\delta$ (CDCl$_3$) 7.23 (2H, d, J=8 Hz), 6.87 (2H, d, J=8 Hz), 6.45 (1H, s), 4.23 (2H, s), 3.80 (3H, s), 2.37 (2H, q, J=7 Hz), 1.80 (1H, s), 1.10 (3H, t, J=7 Hz).

IR: $\nu_{Max}^{CHCl_3}$ 3600, 3450, 2950, 1610, 1510, 1250, 830 cm$^{-1}$.

PREPARATION 31

A mixture of 2-((E)-4-methoxybenzylidene)butan-1-ol (13 g) and manganese dioxide (130 g) in chloroform (600 ml) was stirred at room temperature for 20 hours. Manganese dioxide was filtered off by filtration and the filtrate was condensed to give 2-((E)-4-methoxybenzylidene)butan-1-al (9.4 g).

NMR: $\delta$ (CDCl$_3$) 9.50 (1H, s), 7.90 (1H, s), 7.50 (2H, d, J=9 Hz), 6.97 (2H, d, J=9 Hz), 3.83 (3H, s), 2.60 (2H, q, J=7 Hz), 1.13 (3H, t, J=7 Hz).

IR: $\nu_{Max}^{CHCl_3}$ 2950, 1665, 1600, 1260, 1180, 830 cm$^{-1}$.

PREPARATION 32

Ethyl (E)-4-((E)-4-methoxybenzylidene)-2-hexenate (9 g) was prepared in the substantially same manner as that of Preparation 21 from 2-((E)-4-methoxybenzylidene)-butan-1-al (9 g) and triethyl phosphonoacetate (9.8 g).

NMR: $\delta$ (CDCl$_3$) 7.40 (1H, d, J=16 Hz), 7.33 (2H, d, J=8 Hz), 6.90 (2H, d, J=8 Hz), 6.73 (1H, s), 5.97 (1H, d, J=16 Hz), 4.27 (2H, q, J=7 Hz), 3.83 (3H, s), 2.55 (2H, q, J=7 Hz), 1.33 (3H, t, J=7 Hz), 1.20 (3H, t, J=7 Hz).

IR: $\nu_{Max}^{CHCl_3}$ 2960, 1695, 1600, 1260, 1175, 1035, 850 cm$^{-1}$.

PREPARATION 33

(E)-4-((E)-4-Methoxybenzylidene)-2-hexenoic acid (3.1 g) was prepared in the substantially same manner as that of Preparation 2 from ethyl (E)-4-((E)-4-methoxybenzylidene)-2-hexenate (3.7 g) and 1N sodium hydroxide (20 ml).

NMR: $\delta$ (CDCl$_3$) 10.93 (1H, broad s), 7.53 (1H, d, J=16 Hz), 7.37 (2H, d, J=8 Hz), 6.93 (2J, d, J=8 Hz), 6.80 (1H, s), 6.00 (1H, d, J=16 Hz), 3.85 (3H, s), 2.60 (2H, q, J=7 Hz), 1.23 (3H, t, J=7 Hz).

IR: $\nu_{Max}^{CHCl_3}$ 3400-2400, 1690, 1600, 1255, 1180, 860, 824 cm$^{-1}$.

PREPARATION 34

(E)-4-((E)-4-Methoxybenzylidene)-2-hexenamide (0.7 g) was prepared in the substantially same manner as that of Preparation 4 from (E)-4-((E)-4-methoxybenzylidene)-2-hexenoic acid (1.25 g) and 28% aqueous ammonia (2 ml).

IR: $\nu_{Max}^{CHCl_3}$ 3530, 3500, 3400, 3000, 2950, 1665, 1600, 1585, 1255, 1180, 1030, 845 cm$^{-1}$.

PREPARATION 35

(E,E)-N,N-dimethyl-4-ethyl-2,4-hexadienamide (1.7 g) was prepared in the substantially same manner as that of Preparation 4 from (E,E)-4-ethyl-2,4-hexadienoic acid (2 g) and dimethylamine hydrochloride (2.4 g).

NMR: $\delta$ (CDCl$_3$): 7.2 (1H, d, J=16 Hz), 6.2 (1H, d, J=16 Hz), 5.87 (1H, q, J=7 Hz), 3.03 (6H, s), 2.3 (2H, q, J=7 Hz), 1.77 (3H, d, J=7 Hz), 1.0 (3H, t, J=7 Hz).

IR: $\nu_{Max}^{CHCl_3}$ 3000, 1680, 1640, 1600, 1400 cm$^{-1}$.

PREPARATION 36

To a solution of 4-ethyl-2-hydroxy-5-nitrohexane nitrile (1.7 g) in t-butanol (6.8 ml) was added conc. sulfuric acid (0.8 ml) at 0° C. with stirring. After stirring for an hour at room temperature, the mixture was heated at 75° C. for an hour. The reaction mixture was diluted with water and extracted with ethyl acetate. The extract was washed successively with water and brine, dried over magnesium sulfate, and then evaporated to dryness in vacuo. The resulting oil was dissolved in acetic acid (9 ml) and chromium trioxide (0.82 g) was added thereto. The resulting mixture was heated at 100° C. for 1.5 hours with stirring, concentrated, diluted with water, and then extracted with ethyl acetate. The extract was washed successively with water and brine, and then dried over magnesium sulfate. Removal of the solvent gave an oil which was purified by a preparative thin layer chromatography (solvent: chloroform) to give N-t-butyl-4-ethyl-5-nitro-2-oxo-hexanamide (0.46 g).

NMR: $\delta$ (CDCl$_3$) 6.8 (1H, broad s), 4.7 (1H, m), 3.0 (2H, d, J=6 Hz), 2.7-2.5 (1H, m), 1.7-1.3 (14H, m), 0.9 (3H, m).

IR: $\nu_{Max}^{CHCl_3}$ 3400, 2960, 1715, 1680, 1550, 1520, 1460, 1390, 1370 cm$^{-1}$.

PREPARATION 37

To a solution of 4-ethyl-2-hydroxy-5-nitrohexanamide (0.036 g) in acetic acid (5 ml) was added chromium trioxide (0.25 g). The resulting mixture was heated at 100° C. for 40 minutes with stirring. After cooling, the mixture was evaporated to dryness. The resulting residue was diluted with water and then extracted with ethyl acetate. The extract was washed successively with water, an aqueous sodium bicarbonate and brine, and then dried over magnesium sulfate. The solvent was removed by distillation to give an oil. The oil was purified by a preparative thin layer chromatography [solvent: methanol-chloroform (5:95)] to give 4-ethyl-5-nitro-2-oxo-hexanamide (50 mg).

NMR: $\delta$ (CDCl$_3$) 6.8 (1H, broad s), 5.9 (1H, broad s), 4.7 (1H, m), 3.0 (2H, d, J=6 Hz), 2.5 (1H, m), 1.7-1.2 (5H, m), 0.9 (3H, m).

IR: $\nu_{Max}^{CHCl_3}$ 3550, 3420, 3000, 1710, 1555, 1400 cm$^{-1}$.

PREPARATION 38

Sodium nitrite (0.6 g) was added to a (E,E)-4-ethyl-2,4-hexadienoic acid (0.3 g) in 20% aqueous dioxane (60 ml) with stirring. The mixture was adjusted to pH 3.0. This operation was repeated more twice.

The resulting mixture was extracted with ethyl acetate (50 ml×2) and the combined extracts were washed successively with water. 5% aqueous bicarbonate and brine, and then dried over magnesium sulfate. Removal of the solvent gave 3-ethyl-4-nitro-2-pentenal (0.2 g).

IR: $\nu_{Max}^{CHCl_3}$ 2950, 2850, 2720, 1670, 1550, 1380 cm$^{-1}$.

EXAMPLE 1

Sodium nitrite (60 g) was added to a (E,E)-4-ethyl-2,4-hexadienamide (31.4 g) in 10% aqueous methanol (1500 ml) with stirring, and the mixture was adjusted to pH 3.0 and then stirred at room temperature for 15 minutes. To the resulting reaction mixture was further added sodium nitrite (60 g). The resulting mixture was adjusted to pH 3.0 and then stirred at room temperature for 15 minutes. The resulting reaction mixture was extracted with ethyl acetate (500 ml×3) and the combined extracts were washed with water and brine, respectively, dried over magnesium sulfate and then evaporated to dryness to give a powder. The powder was washed with hot chloroform and then crystallized from methanol to give (E)-4-ethyl-2-hydroxyimino-5-nitro-3-hexenamide (20 g) as colorless prism.

mp: 142° C. (dec.).

NMR: $\delta$(CD$_3$OD) 6.17 (1H, s), 5.32 (1H, q, J=7 Hz), 2.15 (2H, q, J=7 Hz), 1.72 (3H, d, J=7 Hz), 1.0 (3H, t, J=7 Hz).

IR (Nujol): 3500, 3300, 3070, 1660, 1600, 1560, 1390, 1310, 1290, 1200, 1170, 1130, 1100, 1080, 1010, 960, 900, 870, 850, 800 cm$^{-1}$.

EXAMPLE 2

Sodium nitrite (7 g) was added to a (E,E)-N-n-butyl-4-ethyl-2,4-hexadienamide (3 g) in 10% aqueous methanol (300 ml). The resulting mixture was adjusted to pH 3.0 and then stirred at room temperature for 15 minutes. To the resulting reaction mixture was further added sodium nitrite (7 g), and the mixture was adjusted to pH 3 and then stirred at room temperature for 15 minutes. This procedure was repeated more three times. The resulting reaction mixture was extracted twice with ethyl acetate (200 ml×2). The combined extracts were washed successively with water and brine, dried over magnesium sulfate and then evaporated to dryness to give an oil. The oil was column chromatographed on silica gel eluting with chloroform containing 2% methanol to give N-n-butyl-4-ethyl-2-hydroxyimino-5-nitro-3-hexenamide (1.3 g).

NMR: $\delta$ (CDCl$_3$) 6.8 (1H, broad s), 6.1 (1H, s), 5.15 (1H, q, J=7 Hz). 3.5–3.2 (2H, m), 2.12 (2H, q, J=7 Hz), 1.72 (3H, d, J=7 Hz), 1.7–1.3 (4H, m), 1.1–0.9 (6H, m).

IR: $\nu_{max}^{CHCl_3}$: 3410, 3200, 2960, 2930, 2870, 1660, 1550, 1530, 1460, 1380, 1360, 1000 cm$^{-1}$.

EXAMPLE 3

N-Methyl-4-ethyl-2-hydroxyimino-5-nitro-3-hexenamide (0.79 g) was prepared in substantially the same manner as that of Example 2 from (E,E)-N-methyl-4-ethyl-2,4-hexadienamide (1.5 g) and sodium nitrite (12 g).

NMR: $\delta$ (CDCl$_3$) 7.0 (1H, broad s), 6.13 (1H, s), 5.17 (1H, q, J=7 Hz), 2.87 (3H, d, J=5 Hz), 2.12 (2H, q, J=7 Hz), 1.68 (3H, d, J=7 Hz), 0.97 (3H, t, J=7 Hz).

IR: $\nu_{Max}^{CHCl_3}$ 3400, 3200, 2950, 2910, 2850, 1660, 1540, 1450, 1410, 1380, 1340, 1030, 980 cm$^{-1}$.

EXAMPLE 4

1-Formyl-4-(4-ethyl-2-hydroxyimino-5-nitro-3-hexenoyl)piperazine (0.6 g) was prepared in substantially the same manner as that of Example 2 from 1-formyl-4-[(E,E)-4-ethyl-2,4-hexadienoyl]piperazine (1.4 g) and sodium nitrite (12 g).

IR: $\nu_{Max}^{CHCl_3}$ 3250, 3000, 2950, 2900, 1660, 1550, 1460, 1440, 1400, 1360, 1280, 1240, 1200, 1180, 1000 cm$^{-1}$.

EXAMPLE 5

To (E)-4-ethyl-2-hydroxyimino-5-nitro-3-hexenamide (37 mg) in methanol (5 ml) was added excess etheral diazomethane at −20° C. The resulting mixture was allowed to stand at 0° C. for an hour and then acetic acid was added thereto until the yellow color of the solution was discharged. The resulting reaction mixture was evaporated under reduced pressure to give an oil which was purified by preparative thin layer chromatography, developing with chloroform containing 5% methanol to give (E)-4-ethyl-2-methoxyimino-5-nitro-3-hexenamide (21.5 mg).

NMR: $\delta$ (CDCl$_3$) 6.56 (1H, m), 6.08 (1H, s), 5.5 (1H, m), 5.17 (1H, q, J=7 Hz), 4.0 (3H, s), 2.12 (2H, q, J=7 Hz), 1.74 (3H, d, J=7 Hz), 1.02 (3H, t, J=7 Hz).

IR: $\nu_{Max}^{CHCl_3}$ 3540, 3400, 3000, 1690, 1550, 1055 cm$^{-1}$.

EXAMPLE 6

N-(4-Ethyl-2-hydroxyimino-5-nitro-3-hexenoyl)glycine (300 mg) was prepared in the substantially same manner as that of Example 2 from N-[(E,E)-4-ethyl-2,4-hexadienoyl]glycin (800 mg) and sodium nitrite (3 g).

NMR: $\delta$ (CDCl$_3$—CD$_3$OD) 6.2 (1H, s), 5.25 (1H, q, J=7 Hz), 4.0 (2H, s), 2.17 (2H, q, J=7 Hz), 1.75 (3H, d, J=7 Hz), 1.0 (3H, t, J=7 Hz).

IR: $\nu_{Max}^{CHCl_3}$ 1720, 1670, 1550 cm$^{-1}$.

EXAMPLE 7

N-(4-Ethyl-2-hydroxyimino-5-nitro-3-hexenoyl)-piperidine (276 mg) was prepared in the substantially same manner as that of Example 2 from N-[(E,E)-4-ethyl-2,4-hexadienoyl]-piperidine (500 mg) and sodium nitrite (4 g).

NMR: $\delta$ (CDCl$_3$) 6.13 (1H, s), 5.15 (1H, q, J=7 Hz), 3.65 (4H, m), 2.27 (2H, q, J=7 Hz), 1.75 (3H, d, J=7 Hz), 1.7 (6H, m), 1.05 (3H, t, J=7 Hz).

IR: $\nu_{Max}^{CHCl_3}$ 1630, 1550, 1450 cm$^{-1}$.

EXAMPLE 8 t-Butyl bromoacetate (200 μl) was added to a mixture of (E)-4-ethyl-2-hydroxyimino-5-nitro-3-hexenamide (215 mg) and anhydrous potassium carbonate (140 mg) in N,N-dimethylformamide (10 ml). The resulting mixture was stirred at room temperature for an hour, poured into ice-water and then extracted with ethyl acetate. The extract was washed with water, dried over magnesium sulfate and then concentrated to dryness to give a residue (300 mg) which was purified by column chromatography on silica gel to give 2-t-butoxycarbonylmethoxyimino-4-ethyl-5-nitro-3-hexenamide (200 mg).

NMR: δ (CDCl₃—CD₃OD) 6.1 (1H, s), 5.4 (1H, m), 4.6 (2H, s), 2.2 (2H, m), 1.7 (3H, d, J=7 Hz), 1.5 (9H, s), 1.05 (3H, t, J=9 Hz).

IR: $\nu_{Max}^{CHCl_3}$ 3500, 3400, 2950, 2900, 1735, 1680, 1540, 1450, 1365, 1220, 1150, 1090, 1020, 940, 920, 840 cm⁻¹.

EXAMPLE 9

2-t-Butoxycarbonylmethoxyimino-4-ethyl-5-nitro-3-hexenamide (80 mg) was treated with trifluoroacetic acid (1 ml) at ambient temperature for 2 hours. Excess trifluoroacetic acid was distilled off under reduced pressure to give a residue which was purified by preparative thin layer chromatography, eluting with a mixture of benzene, dioxane and acetic acid (14:5:1) to give 2-carboxymethoxyimino-4-ethyl-5-nitro-3-hexanamide (32 mg).

NMR: δ (CD₃OD) 6.2 (1H, s), 5.4 (1H, t, J=7 Hz), 4.7 (2H, s), 2.2 (2H, q, J=7 Hz), 1.7 (3H, d, J=7 Hz), 1.05 (3H, t, J=7 Hz).

EXAMPLE 10

N-(4-Ethyl-2-hydroxyimino-5-nitro-3-hexenoyl)-L-threonine (180 mg) was prepared in the substantially same manner as that of Example 2 from N-[(E,E)-4-ethyl-2,4-hexadienoyl]-L-threonine (600 mg) and sodium nitrite (4 g).

NMR: δ (CDCl₃—CD₃OD) 6.2 (1H, s), 5.3 (1H, q, J=7 Hz), 4.8–4.0 (2H, m), 2.2 (2H, q, J=7 Hz), 1.7 (3H, d, J=7 Hz), 1.3 (3H, m), 1.0 (3H, d, J=7 Hz).

EXAMPLE 11

N-Benzyl-4-ethyl-2-hydroxyimino-5-nitro-3-hexenamide (340 mg) was prepared in the substantially same manner as that of Example 2 from (E,E)-N-benzyl-4-ethyl-2,4-hexadienamide (1 g) and sodium nitrite (4 g).

NMR: δ (CDCl₃—CD₃OD) 7.3 (5H, s), 6.2 (1H, s), 5.2 (1H, q, J=7 Hz), 4.5 (2H, d, J=5 Hz), 2.18 (2H, q, J=7 Hz), 1.8 (3H, d, J=7 Hz), 1.0 (3H, d, J=7 Hz).

EXAMPLE 12

2-Hydroxyimino-4-methyl-5-nitro-3-hexenamide (180 mg) was prepared in the substantially same manner as that of Example 2 from (E,E)-4-methyl-2,4-hexadienamide (200 mg) and sodium nitrite (1500 mg).

NMR: δ (CD₃OD) 6.22 (1H, s), 5.30 (1H, q, J=7 Hz), 1.68 (3H, s), 1.68 (3H, d, J=7 Hz).

IR (Nujol): 3450, 3250, 2950, 1680, 1620, 1600, 1550, 1460, 1380, 1370, 1000 cm⁻¹.

EXAMPLE 13

2-Hydroxyimino-4-methyl-5-nitro-5-pentenamide (120 mg) was prepared in the substantially same manner as that of Example 2 from (E)-4-methyl-2,4-pentadienamide (200 mg) and sodium nitrite (1500 mg).

NMR: δ (CD₃OD) 6.23 (1H, s), 5.15 (2H, s), 2.07 (3H, s).

IR: $\nu_{Max}^{CHCl_3}$ 3500, 3300, 2950, 1680, 1555, 1380 cm⁻¹.

EXAMPLE 14

4-Ethyl-2-hydroxyimino-5-(4-methoxyphenyl)-5-nitro-3-pentenamide (210 mg) was prepared in the substantially same manner as that of Example 2 from (E)-4-((E)-4-methoxybenzylidene)-2-hexenamide (500 mg) and sodium nitrite (3 g).

NMR: δ (CDCl₃) 7.40 (2H, d, J=8 Hz), 6.87 (2H, d, J=8 Hz), 6.86 (2H, m), 6.23 (1H, s), 6.23 (1H, m), 5.90 (1H, s), 3.77 (3H, s), 2.03 (2H, q, J=7 Hz), 0.97 (3H, t, J=7 Hz).

IR: $\nu_{Max}^{CHCl_3}$ 3550, 3420, 3000, 1695, 1620, 1560, 1365, 1260, 1040.

EXAMPLE 15

N-[4-Ethyl-2-hydroxyimino-5-nitro-3-hexenoyl]-4-aminobutyric acid (100 mg) was prepared in the substantially same manner as that of Example 2 from N-[(E,E)-4-ethyl-2,4-hexadienoyl]-4-aminobutyric acid (270 mg) and sodium nitrite (2 g).

NMR: δ (CDCl₃—CD₃OD) 6.2 (1H, s), 5.2 (1H, m), 3.5 (2H, m), 2.6–1.9 (6H, m), 1.75 (3H, d, J=7 Hz), 1.0 (3H, t, J=7 Hz).

EXAMPLE 16

4-Ethyl-2-hydroxyimino-5-methyl-5-nitro-3-hexenamide (740 mg) was prepared in the substantially same manner as that of Example 2 from (E)-4-ethyl-5-methyl-2,4-hexadienamide (1 g) and sodium nitrite (6 g).

NMR: δ (CDCl₃—CD₃OD) 6.2 (1H, s), 2.15 (2H, q, J=7 Hz), 1.8 (6H, s), 0.95 (3H, t, J=7 Hz).

IR: $\nu_{Max}^{Nujol}$ 3450, 1650, 1590, 1540 cm⁻¹.

EXAMPLE 17

4-Ethyl-2-hydroxyimino-5-nitro-3-hexenenitrile (3.9 g) was prepared in the substantially same manner as that of Example 2 from (E,E)-4-ethyl-2,4-hexadiene-nitrile (3 g) and sodium nitrite (12 g).

IR: $\nu_{Max}^{CHCl_3}$ 3550, 3250, 3000, 2250, 1640, 1550, 1460, 1390, 1360, 1040 cm⁻¹.

EXAMPLE 18

4-Ethyl-2-hydroxyimino-5-nitro-3-hexenal (100 mg) was prepared in the substantially same manner as that of Example 2 from (E,E)-4-ethyl-2,4-hexadienal (0.3 g) and sodium nitrite (1.8 g).

NMR: δ (CDCl₃) 9.53 (1H, s), 6.03 (1H, s), 5.23 (1H, q, J=7 Hz), 2.15 (2H, q, J=7 Hz), 1.77 (3H, d, J=7 Hz), 1.05 (3H, t, J=7 Hz).

IR: $\nu_{Max}^{CHCl_3}$ 3550, 3250, 3000, 1700, 1610, 1550, 1460, 1390, 1360, 1040 cm⁻¹.

EXAMPLE 19

Ethyl 4-ethyl-2-hydroxyimino-5-nitro-3-hexenoate (110 mg) was prepared in the substantially same manner as that of Example 2 from ethyl (E,E)-4-ethyl-2,4-hexadienoate (0.3 g) and sodium nitrite (1.8 g).

NMR: δ (CDCl₃) 10.3 (1H, broad s), 6.17 (1H, s), 5.23 (1H, q, J=7 Hz), 4.3 (2H, q, J=7 Hz), 2.13 (2H, q, J=7 Hz), 1.73 (3H, d, J=7 Hz), 1.33 (3H, t, J=7 Hz), 1.0 (3H, t, J=7 Hz).

IR: $\nu_{Max}^{CHCl_3}$ 3570, 3250, 3000, 1725, 1555, 1390, 1030 cm⁻¹.

EXAMPLE 20

Methyl 2-[4-ethyl-2-hydroxyimino-5-nitro-3-hexenoylamino]acetate (120 mg) was prepared in the substantially same manner as that of Example 2 from methyl 2-[(E,E)-4-ethyl-2,4-hexadienoylamino]acetate (0.3 g) and sodium nitrite (1.8 g).

NMR: δ (CDCl₃) 10.2 (1H, broad s), 7.42 (1H, broad s), 6.13 (1H, s), 5.2 (1H, q, J=7 Hz), 4.12 (2H, d, J=6 Hz), 3.73 (3H, s), 2.12 (2H, q, J=7 Hz), 1.7 (3H, d, J=7 Hz), 0.97 (3H, t, J=7 Hz).

IR: $\nu_{Max}^{CHCl_3}$ 3570, 3400, 3000, 1740, 1680, 1555, 1440, 1390, 1230 cm⁻¹.

EXAMPLE 21

Hydroxylamine hydrochloride (69.5 mg) was added to a solution of 4-ethyl-2-hydroxyimino-5-nitro-3-hexenal (100 mg) in a mixture of chloroform (3 ml) and methanol (2 ml) with stirring at room temperature. The resulting mixture was stirred at the same temperature overnight and evaporated to dryness. The residue was washed successively with water, aqueous sodium bicarbonate solution and brine, and dried over magnesium sulfate. The solvent was distilled under reduced pressure to give a residue which was purified by preparative thin layer chromatography [solvent: methanol-chloroform (10:90)] to give 4-ethyl-2-hydroxyimino-5-nitro-3-hexenaldehyde oxime (65 mg).

NMR: δ (CDCl$_3$—CD$_3$OD) 7.77 (1H, s), 6.08 (1H, s), 5.23 (1H, q, J=7 Hz), 2.15 (2H, q, J=7 Hz), 1.73 (3H, d, J=7 Hz), 1.0 (3H, t, J=7 Hz).

IR: $\nu_{Max}^{Nujol}$ 3250, 2400, 1650, 1550, 960 cm$^{-1}$.

EXAMPLE 22

To a solution of 4-ethyl-2-hydroxyimino-5-nitro-3-hexenal (100 mg) in dry ethanol (10 ml) was added sodium borohydride (15 mg) at 0° C. with stirring. The resulting mixture was stirred at the same temperature for 10 minutes and 1N hydrochloric acid was added thereto. The reaction mixture was extracted with ethyl acetate and the extract was washed with successively with water, an aqueous sodium bicarbonate solution and brine, dried over magnesium sulfate, and then evaporated to dryness in vacuo to give an oil. The oil was purified by a preparative thin layer chromatography [solvent: methanol-chloroform (10:90)] to give 4-ethyl-2-hydroxyimino-5-nitro-3-hexen-1-ol (80 mg).

NMR: δ (CDCl$_3$—CD$_3$OD) 6.17 (1H, s), 5.23 (1H, q, J=7 Hz), 4.23 (2H, s), 2.23 (2H, q, J=7 Hz), 1.73 (3H, d, J'7 Hz), 1.05 (3H, t, J=7 Hz).

IR: $\nu_{Max}^{CHCl_3}$ 3600, 3300, 3000, 1555, 1460, 1390, 1360 cm$^{-1}$.

EXAMPLE 23

1-Acetoxy-4-ethyl-2-hydroxyimino-5-nitro-3-hexene (60 mg) was prepared in the substantially same manner as that of Example 2 from (E,E)-1-acetoxy-4-ethyl-2,4-hexadiene (0.3 g) and sodium nitrite (1.8 g).

IR: $\nu_{Max}^{CHCl_3}$ 3600, 3300, 3000, 1740, 1550, 1390, 1220 cm$^{-1}$.

EXAMPLE 24

Hydroxylamine hydrochloride (60 mg) was added to a solution of N-t-butyl-4-ethyl-5-nitro-2-oxo-hexanamide (100 mg) in a mixture of chloroform (1.5 ml) and methanol (1 ml). The resulting mixture was stirred at room temperature overnight.

The reaction mixture was evaporated and the resulting residue was diluted with ethyl acetate. The resulting solution was washed successively with water and brine, dried over magnesium sulfate and then evaporated to dryness. The resulting oil was purified by a preparative thin layer chromatography [solvent: benzene-ethyl acetate (10:1)] to give N-t-butyl-4-ethyl-2-hydroximino-5-nitrohexanamide (47 mg).

NMR: δ (CDCl$_3$) 9.1 (1H, broad s), 6.7 (1H, broad s), 4.55 (1H, m), 2.8–2.4 (3H, m), 1.7–1.2 (14H, m), 0.9 (3H, m).

IR: $\nu_{Max}^{CHCl_3}$ 3600, 3410, 3300, 3000, 1670, 1630, 1550, 1530, 1400, 1240, 1000 cm$^{-1}$.

EXAMPLE 25

4-Ethyl2-hydroxyimino-5-nitro-hexanamide (15 mg) was prepared in the substantially same manner as that of Example 24 from 4-ethyl-5-nitro-2-oxo-hexanamide (20 mg) and hydroxylamine hydrochloride (14 mg).

NMR: δ (CDCl$_3$) 9.0 (1H, broad s), 6.7 (1H, broad s), 5.6 (1H, broad s), 4.55 (1H, m), 2.8–2.4 (3H, m), 1.7–1.2 (5H, m), 0.9 (3H, m).

IR: $\nu_{Max}^{CHCl_3}$ 3550, 3425, 3300, 3000, 1690, 1555, 1400, 1000 cm$^{-1}$.

EXAMPLE 26

4-Ethyl-2-hydroxyimino-3-methyl-5-nitro-3-hexenamide (170 mg) was prepared in the substantially same manner as that of Example 2 from (E,E)-4-ethyl-3-methyl-2,4-hexadienamide (400 mg) and sodium nitrite (1600 mg).

NMR: δ (CD$_3$OD) 5.68 (1H, q, J=7 Hz), 2.00 (2H, q, J=7 Hz), 1.92 (3H, s), 1.66 (3H, d, J=7 Hz), 0.90 (3H, t, J=7 Hz).

IR: $\nu_{Max}^{Nujol}$ 3500, 3290, 3240, 3170, 1670, 1600, 1555 cm$^{-1}$.

EXAMPLE 27

N,N-Dimethyl-4-ethyl-2-hydroxyimino-5-nitro-3-hexenamide (203 mg) was prepared in the substantially same manner as that of Example 2 from (E,E)-N,N-dimethyl-2,4-hexadienamide (0.3 g) and sodium nitrite (1.8 g).

IR: $\nu_{Max}^{CHCl_3}$ 3570, 3250, 3000, 1640, 1550, 1380 cm$^{-1}$.

EXAMPLE 28

Hydroxylamine hydrochloride (100 mg) was added to a solution of 3-ethyl-4-nitro-2-pentenal (100 mg) in chloroform (3 ml) and methanol (2 ml) with stirring. The resulting mixture was stirred at room temperature overnight. The reaction mixture was evaporated to dryness and the residue was diluted with water and extracted with ethyl acetate (50 ml×2).

The combined extracts were washed successively with water, 5% sodium bicarbonate and brine, and then dried over magnesium sulfate. Removal of the solvent gave an oil which was purified by a preparative thin layer chromatography (5% methanol-chloroform) to give 3-ethyl-4-nitro-2-pentenal oxime (80 mg).

IR: $\nu_{Max}^{CHCl_3}$ 3550, 3250, 2950, 1550, 1380 cm$^{-1}$.

We claim:

1. A compound of the formula or its pharmaceutically acceptable salt:

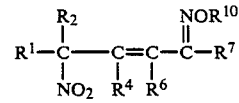

wherein

R$^1$ is hydrogen, lower alkyl, or lower alkoxyphenyl,
R$^2$ is hydrogen or lower alkyl,
R$^4$ is lower alkyl,
R$^6$ is hydrogen or lower alkyl,
R$^7$ is hydrogen, hydroxyiminomethyl, cyano, formyl-piperazinecarbonyl, alkanoyl, or esterified carboxy, and
R$^{10}$ is hydrogen or lower alkyl which may have carboxy or esterified carboxy.

2. A method of treating coronary insufficiency which comprises administering to a subject in need of such treatment an effective amount of the compound of claim 1.

3. A method of treating angina pectoris, which comprises administering to a subject in need of such treatment an effective amount of the compound of claim 1.

4. A method of treating myocardial infarction which comprises administering to a subject in need of such treatment an effective amount of the compound of claim 1.

5. A method of treating hypertension which comprises administering to a subject in need of such treatment an effective amount of the compound of claim 1.

6. A method of treating cerebral apoplexy which comprises administering to a subject in need of such treatment an effective amount of the compound of claim 1.

7. A method of treating thrombosis which comprises administering to a subject in need of such treatment an effective amount of the compound of claim 1.

8. A method of treating pulmonary embolism which comprises administering to a subject in need of such treatment an effective amount of the compound of claim 1.

9. A compound according to claim 1, wherein $R^{10}$ is hydrogen.

10. A compound according to claim 1, wherein $R^1$ is lower alkyl, $R^2$ is hydrogen, $R^4$ is lower alkyl, $R^6$ is hydrogen and $R^{10}$ is hydrogen.

11. A compound according to claim 1 wherein $R^1$ is methyl, $R^2$ is hydrogen, $R^4$ is ethyl, $R^6$ is hydrogen and $R^{10}$ is hydrogen.

12. A pharmaceutical antithrombotic and antihypertensive composition comprising an effective amount of a compound as defined in claim 1 or its pharmaceutically acceptable salt in association with a pharmaceutically acceptable carrier or excipient.

* * * * *

UNITED STATES PATENT AND TRADEMARK OFFICE
CERTIFICATE OF CORRECTION

PATENT NO.   : 4,863,926
DATED        : SEPTEMBER 5, 1989
INVENTOR(S)  : MASANORI OKAMOTO ET AL.

It is certified that error appears in the above-identified patent and that said Letters Patent is hereby corrected as shown below:

ON TITLE PAGE:

In the inventors, delete "Konsaka" and insert --Kohsaka--.

Signed and Sealed this

Nineteenth Day of November, 1991

Attest:

HARRY F. MANBECK, JR.

*Attesting Officer*          *Commissioner of Patents and Trademarks*